(12) United States Patent
DeAngelis

(10) Patent No.: US 6,189,459 B1
(45) Date of Patent: Feb. 20, 2001

(54) COLLAPSIBLE AUXILIARY INSTRUMENT SHELF FOR USE IN SURGICAL OPERATING ROOMS

(76) Inventor: Luciano S. DeAngelis, 330 Bartlett Blvd. Suite 2102, El Paso, TX (US) 79912

( * ) Notice: Under 35 U.S.C. 154(b), the term of this patent shall be extended for 0 days.

(21) Appl. No.: 09/457,504

(22) Filed: Dec. 8, 1999

Related U.S. Application Data (60) Provisional application No. 60/111,450, filed on Dec. 8, 1998.

(51) Int. Cl.⁷ .................................................. A47B 9/20
(52) U.S. Cl. .................................... 108/96; 108/147.21
(58) Field of Search .............................. 108/96, 92, 95, 108/147, 144.11, 147.21, 147.12, 147.15, 90; 248/243, 241, 240.4, 125.1, 125.8, 161, 162.1, 157

(56) References Cited

U.S. PATENT DOCUMENTS

| | | |
|---|---|---|
| D. 141,593 | 6/1945 | Doty . |
| 270,443 | 1/1883 | Kraemer . |
| 912,035 | 2/1909 | Schaefle . |
| 1,624,862 | 4/1927 | Elliot . |
| 1,640,440 * | 8/1927 | Conrad .................................. 108/95 |
| 1,650,293 | 11/1927 | Morey et al. . |
| 1,683,228 * | 9/1928 | Armstrong ............................. 108/96 |
| 1,715,076 | 5/1929 | Schmidt et al. . |
| 1,802,362 * | 4/1931 | Walter .................................. 108/96 |
| 3,113,531 * | 12/1963 | Barnard ............................. 108/96 X |
| 3,184,207 * | 5/1965 | Hermanns et al. ......... 108/147.21 X |
| 3,905,311 * | 9/1975 | Carpentier ....................... 108/147 X |
| 3,971,568 | 7/1976 | Wright . |
| 4,488,497 * | 12/1984 | Bevans ............................ 108/147.21 |
| 4,504,073 | 3/1985 | Isaacs . |
| 4,627,363 | 12/1986 | Jones . |
| 4,948,154 | 8/1990 | Guggenheim . |
| 4,998,742 | 3/1991 | Maynard . |
| 5,379,703 | 1/1995 | Marshall . |
| 5,436,053 | 7/1995 | Herum . |
| 5,642,898 | 7/1997 | Wise . |
| 5,713,584 | 2/1998 | Crane . |
| 5,931,102 * | 8/1999 | Grahl ......................... 108/147.21 X |

\* cited by examiner

Primary Examiner—Jose V. Chen
(74) Attorney, Agent, or Firm—Rod D. Baker (57) ABSTRACT

An auxiliary shelf that can be attached to existing operating room carts to provide additional sterile space upon which instruments may be placed for access during surgery. The auxiliary shelf is located above the main shelf area of the cart. The auxiliary shelf can be swivelled between a collapsed position parallel against the back of the cart when not in use to permit storage of the cart in less space. The vertical position of the shelf can be adjusted, and a lift assist is provided to reduce the effort required to raise the auxiliary shelf from the lower collapsed storage position to the horizontal use position above the main shelf of the cart. There also is provided special custom drape for placement upon the auxiliary shelf to provide a sterile covering for the auxiliary shelf. The drape includes several special features which permit it to be handled, placed upon the auxiliary shelf, and secured in place with minimal challenges to sterility and to maintain the sterile filed in the operating room.

14 Claims, 9 Drawing Sheets

COLLAPSIBLE AUXILIARY INSTRUMENT SHELF FOR USE IN SURGICAL OPERATING ROOMS

CROSS-REFERENCE TO RELATED APPLICATIONS

This application claims the benefit of the filing of Provisional Application Serial No. 60/111,450, entitled "Collapsible Auxiliary Shelf for Use in Surgical Operating Rooms", filed on Dec. 8, 1998, and the specification thereof is incorporated herein by reference.

BACKGROUND OF THE INVENTION

1. Field of the Invention (Technical Field)

The present invention relates to specialized tables, particularly to tables or carts used in surgical operating rooms, and specifically to an instrument shelf for use on carts to promote efficient and organized availability of surgical tools while optimizing the maintenance of a sterile field in the operating room.

2. Background Art

During even moderately complicated surgery, the surgeon must have rapid access to numerous surgical instruments. To this end, the instruments are disposed upon a sterilized wheeled cart (or sometimes a wheelless table) situated in the operating room. The cart has one or more shelves upon which the surgical instruments are placed.

In complex surgeries, so many instruments may be required that more than one shelf are required to hold all the instruments for ready use. Accordingly, presently in the art, more than one cart may be used, which crowds the operating room and complicates efforts to maintain the sterility of the operating area. Alternatively, operating room personnel may place instruments upon more than one tray, and then stack the trays one upon another on a single cart, which unfortunately complicates access to the instruments. Un-stacking and re-stacking trays of instruments upon a single cart takes too much time and increases the possibility of mishaps. Nevertheless, there is a need for rapid and ready access to all the instruments, without needlessly cramping the work area in the operating room with multiple carts—especially in smaller operating rooms.

Various attempts have been made to improve the stability, compactness, and facility of carts and tables in the furniture art generally, such as by providing various shelves and collapsing shelf arrangements, and modes of improving cart stability and adjustability. Examples of previous efforts include U.S. Pat. No. 4,998,742 to Maynard; U.S. Pat. No. 4,504,073 to Isaacs; U.S. Pat. No. 1,715,076 to Schmidt et al.; U.S. Pat. No. 1,624,862 to Elliot, et al.; and U.S. Pat. No. 1,650,293 to Morey et al. None of these prior efforts were specifically directed at solving the problems unique to carts and tables used in surgical operating rooms, and leave those problems unresolved.

Another challenge in surgical operating rooms is the preservation of the sterile field. It is known to provide covers for hospital gurneys and tables, such as the cover shown in U.S. Pat. No. 5,436,053 to Herum, and to provide some means for securing a cover to a table, such as that disclosed in U.S. Pat. No. 4,627,363 to Jones. Nevertheless, a significant need remains for a drape for covering tables and carts, that is specially suited for the special needs and demands of the operating room. Against the foregoing background, the present invention was developed.

SUMMARY OF THE INVENTION (DISCLOSURE OF THE INVENTION)

The invention relates to an auxiliary shelf that can be attached to existing operating room carts to provide additional sterile space upon which instruments may be placed for access during surgery. The auxiliary shelf is located above the main shelf are of the cart. The auxiliary shelf can be swivelled between a collapsed position parallel against the back of the cart when not in use to permit storage of the cart in less space. The vertical position of the shelf can be adjusted, and a lift assist is provided to reduce the effort required to raise the auxiliary shelf from the lower collapsed storage position to the horizontal use position above the main shelf of the cart. There also is provided according to the invention a special custom drape for placement upon the auxiliary shelf to provide a sterile covering for the auxiliary shelf. The drape includes several special features which permit it to be handled, placed upon the auxiliary shelf, and secured in place with minimal challenges to sterility and to maintain the sterile filed in the operating room. There also is disclosed a retractable step stair that is easily operated by the user's foot. The step stair allows personnel to step up to the elevated auxiliary shelf. The step stair can be deployed or retracted for storage under the cart without having to by touched by the user's hands, another advantage promoting sterility of the operating room sterile field.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (BEST MODES FOR CARRYING OUT THE INVENTION)

The present invention permits operating room personnel rapid and easy access to numerous instruments, without compromising sterility, by providing a dual-shelf cart. An upper shelf is disposed above, and somewhat horizontally offset from, the main shelf, the main shelf essentially being the top of the wheeled cart or table. The upper shelf provides an entire second surface upon which instruments may be arrayed, and yet because it is offset horizontally rearward, it does not impede the user's access to or visibility of the instruments situated upon the bottom or main shelf.

Among the advantages of the invention is its versatility. First, the invention is adaptable for use upon a variety of pre-existing carts and tables. Through the use of an adjustable clamp, the invention may be removably attached to existing instrument carts and tables, thereby avoiding the need to replace current equipment inventories. The apparatus of the invention also is versatile in that it may be quickly and easily folded away when not in use. Thus, the auxiliary shelf can be folded down into an innocuous position while the main shelf is used during less complicated surgeries. Also, when the auxiliary shelf according to the invention is folded down, the cart or table occupies less space and is therefore much more conveniently and easily stored.

Also disclosed is a custom drape specially adapted for use with the auxiliary shelf apparatus of the invention. The custom drape is specially constructed to guard against instrument "strike-throughs" which may compromise the sterile field of the operating room. Thus, the auxiliary shelf according to the invention may be used without breaching standard operating room sterility protocols.

Figure 1:
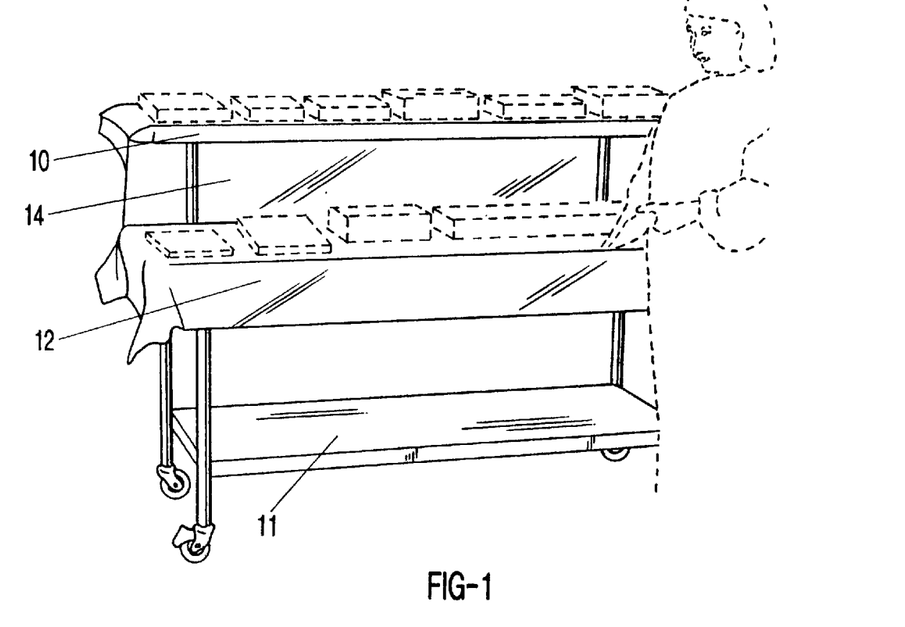
FIG. 1 is a perspective front view of the auxiliary shelf apparatus of the invention, shown in use upon a conventional operating room cart and with a variety of operating instruments resting thereon.
Figure 2:
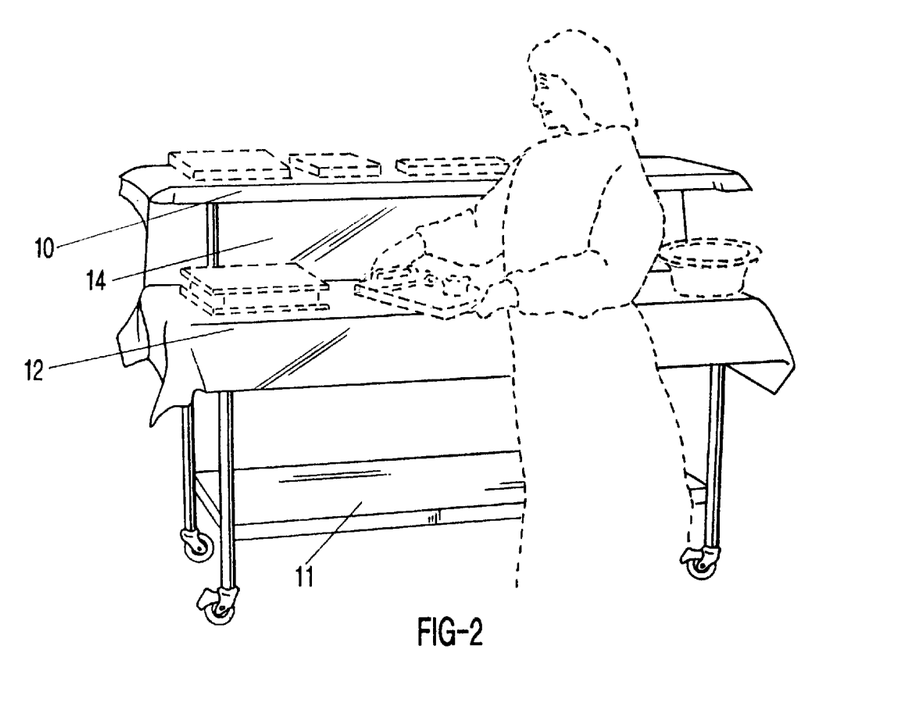
FIG. 2 is another perspective front view of the embodiment shown in FIG. 1.
Figure 3:
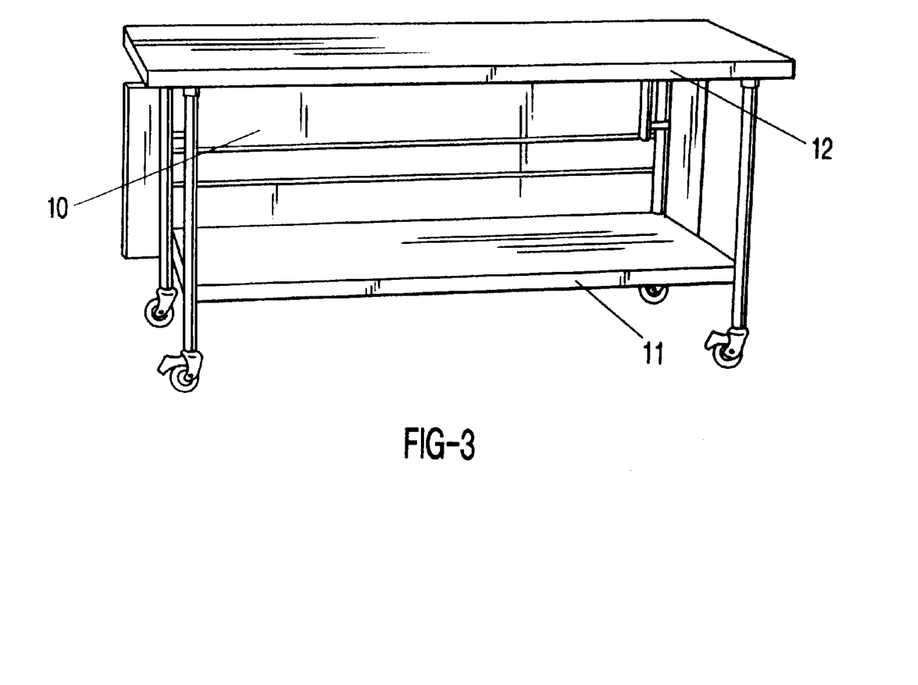
FIG. 3 is another perspective front view of the embodiment shown in FIG. 1, depicting the auxiliary shelf in the collapsed storage position at the back of the cart.
Figure 4:
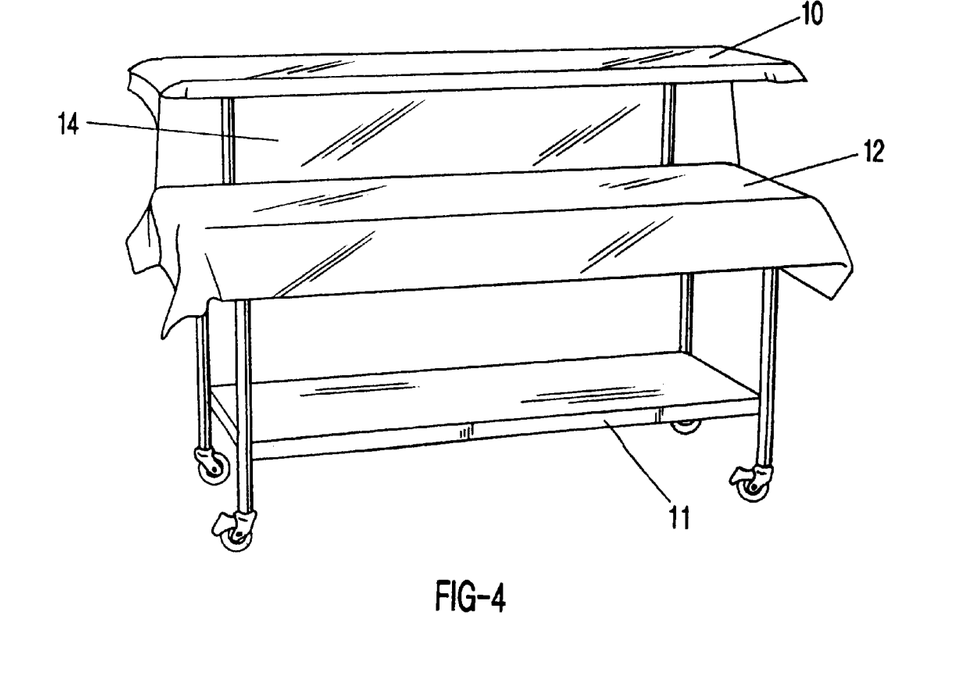
FIG. 4 is a perspective front view of the embodiment shown in FIG. 1, showing the sterile drape according to the invention in place upon the auxiliary shelf.

FIG. 1 shows the auxiliary shelf 10 according to the invention mounted upon an existing stock operating room cart 11. The illustration shows the paper and clear plastic drape 14 custom-fitted to the auxiliary shelf 10 and used to maintain the integrity of the sterile field. Various surgical instruments are visible situated upon both the auxiliary shelf 10 and the main shelf 12 of the stock cart 11. FIG. 2 shows how surgical instruments upon the stock cart 11 are readily accessible to operating room personnel, with the inventive auxiliary shelf 10 conveniently located above the main shelf 12 portion of the stock cart 11. FIG. 3 shows the auxiliary shelf 10 in the collapsed position, folded down to be disposed vertically and below the main shelf 12, closely adjacent to the back of the cart 11. FIG. 4 shows the inventive auxiliary shelf 10 and main shelf 12 draped with sterile drapes, including the custom-fitted drape 14 upon the auxiliary shelf 10, in position to receive thereon the instruments to be used.

Figure 5:
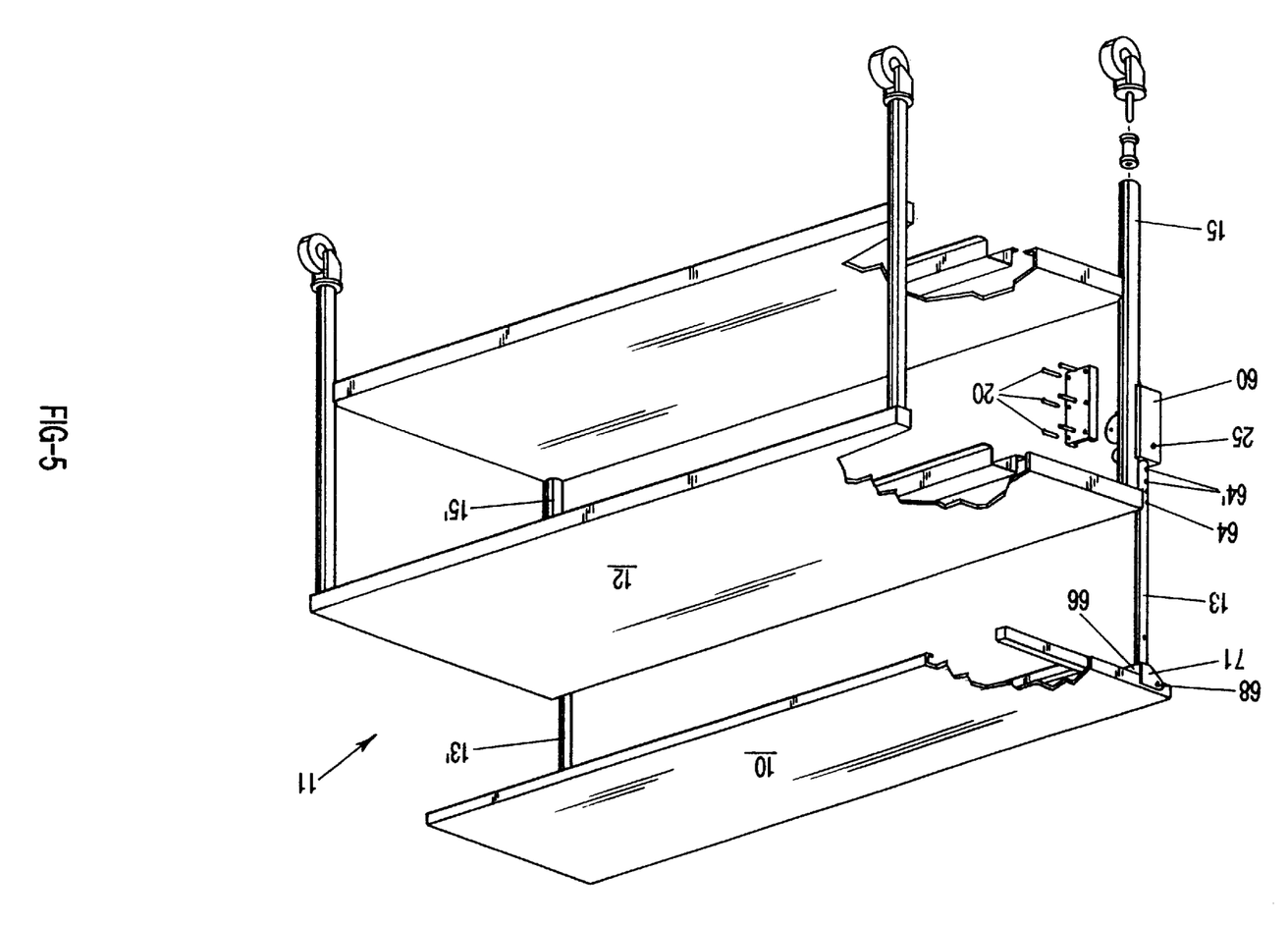
FIG. 5 is a perspective, partially exploded front view of the embodiment shown in FIG. 1, depicting additional details and with portions broken away to reveal manufacture design.
Figure 6:
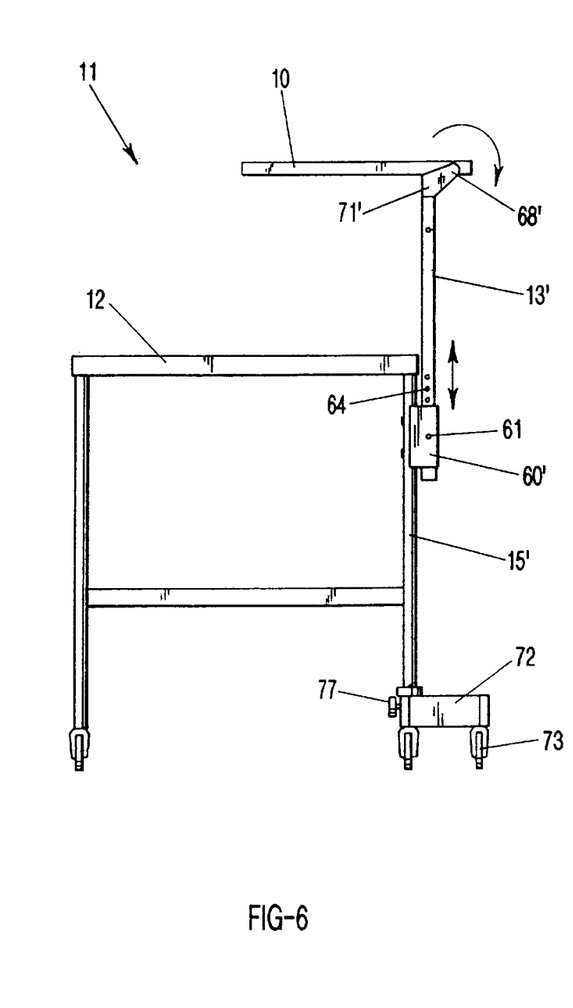
FIG. 6 is a right side view of the embodiment shown in FIG. 5, showing the auxiliary shelf in the use position.
Figure 7:
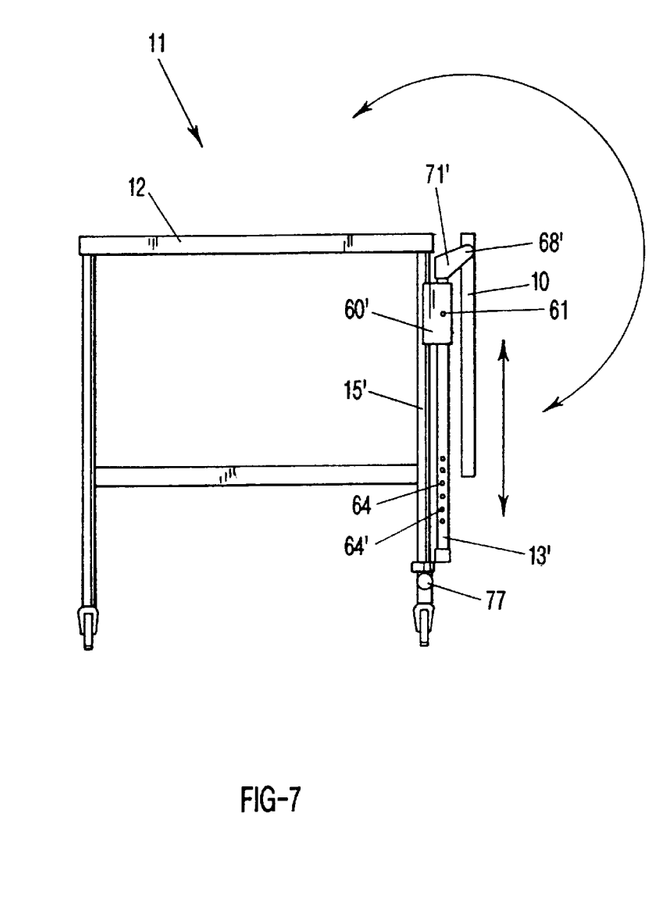
FIG. 7 is a right side view of the embodiment shown in FIG. 5, depicting the auxiliary shelf in the collapsed storage position.
Figure 8:
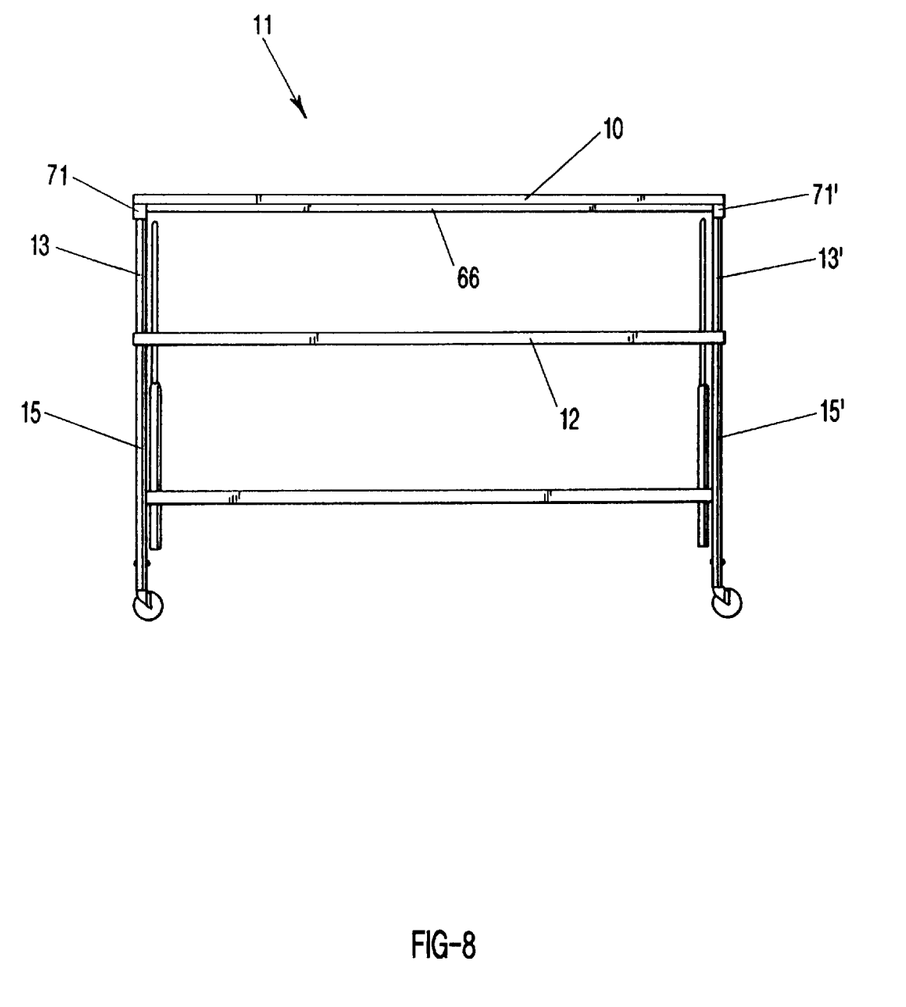
FIG. 8 is a front view of the embodiment shown in FIG. 6.

FIGS. 5–8 illustrate the invention having the advantageous auxiliary shelf 10 that can be both raised and lowered, as well as pivoted, to foster adjustability of position as well as ease of storage of the cart 11 when not in use. FIG. 16 is a side view of the apparatus in the in-use position, with the auxiliary shelf 10 in a horizontal in use and elevated position. Combined reference to FIGS. 6–8 shows how the auxiliary shelf legs 13, 13' are slidably attached to the rear legs 15, 15' of the main cart 11 by means of a pair of corresponding clamp blocks 60, 60'. Each of the clamp blocks 60, 60' has an axial bore there through, through which a corresponding one of the auxiliary shelf rear legs 13, 13' is vertically slidably disposed. Clamp blocks are fixedly connected to the rear legs 15, 15' of the cart 11, such that their axial bores are essentially vertical. The gliding motion of the legs 13, 13' in the clamp blocks 60, 60' is promoted by a pair of lubricated bearings, such as Teflon® bearings, disposed within the bore of each clamp block 60, or 60'. Alternative types of bearings, such as convention linear bearings, may also provide for the smooth sliding motion of the legs 13'13' with respect tho the clamp blocks 60, 60'.

FIGS. 5 and 6 illustrate the inventive auxiliary shelf 10 in the "in-use" position. The auxiliary shelf legs 13, 13' are securely but removably attached to the rear legs 15, 15' of the stock cart 11 by means of a pair of screw- or bolt-actuated mounting clamps 60, 60'. Shelf legs 13, 13' preferably are fashioned from solid stainless steel rods. Only one mounting clamp assembly 60 is depicted in FIG. 5, but a second substantially identical mounting clamp assembly 60' (FIG. 6) is employed to connect the auxiliary shelf leg 13' to rear leg 15' of the stock cart 11. Description of the construction, function, and operation of one of the mounting clamps 60 thus serves to describe the other clamp 60' of the pair. As indicated by FIG. 5, screws or bolts 20 draw the two portions of the mounting clamp 60 tightly together and against the stock cart rear leg 15 thereby to secure the clamp 60 in position upon the rear leg, immobile unless and until the screws are later loosened to provide for removal or adjustment of the shelf 10.

Figure 5A:
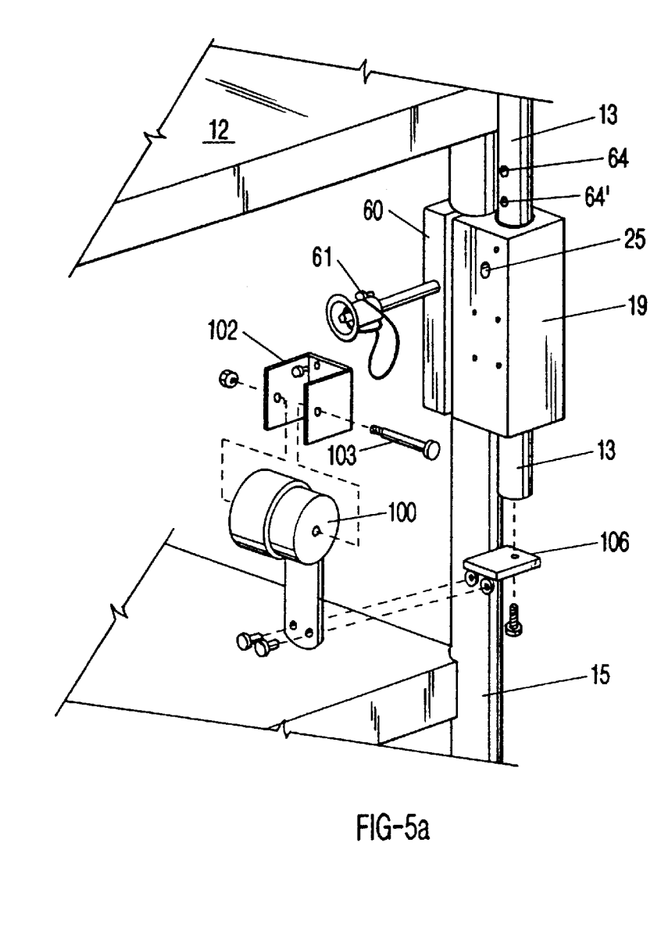
FIG. 5A is an enlarged exploded view of a portion of the embodiment shown in FIG. 5.

FIG. 5A also best illustrates the configuration of the mounting clamp 60 . Mounting clamp 60 has a pair of clamp members, including a housing 19. The clamping members are disposable on either side of the rear leg 15 of an existing cart or table, and a plurality of threaded clamping screws or bolts 20 are tightened in holes (corresponding holes in second clamping member housing 19 not shown) to draw the clamping members toward each other thereby to grip the rear leg 15 or 15' of the existing table or cart 11.

FIG. 5A also shows that the rearward housing portion 19 of the mounting clamp 60 has a vertical, cylindrical bore there-through in which the corresponding shelf leg 13 is slidably received. The diameter of the housing passage is only slightly larger than the diameter of the shelf leg 13, so that the shelf leg 13 can slide smoothly up and down in the housing 19 of the mounting clamp 60, yet shelf leg 13 is maintained against any movement or shifting besides upand-down translation generally parallel to the rear leg 15 of the cart 11. The smooth axial movement of the shelf leg 13 in the housing 19 is promoted by the use of self-lubricating bushings (not shown) mounted within the housing passage adjacent its openings at the top and bottom of the housing 19. The housing 19 of the mounting clamp 60 has an aperture 25 therein, and the shelf leg 13 also has a plurality (e.g. six) of uniformly spaced holes 64, 64' there through along a portion of its length in the vicinity of the clamp 60. A quick-release pin 61 having a length at least equaling the width of the housing 19 is insertable through the aperture 25 and any one of the holes 64, 64' in the shelf leg 13. Any of the holes 64, 64' is alignable with the aperture 25 in the housing 19, and the quick-release pin 61 is insertable into the aligned aperture and hole 64 to fix the vertical position of the shelf leg 13 and thus the height of the shelf 10. By removing the pin 61 and selectively aligning one of the holes 64, 64' with the aperture 25 and re-inserting the pin through the aperture and selected hole in a conventional manner, the operator can suitably adjust of the height of the auxiliary shelf 10 above the main shelf 12. The holes 64, 64' in the shelf legs 13, 13' optionally but preferably have chamfered openings to promote self-alignment of the pin 61 through the aperture 25 and into the selected one of the holes 64, 64'.

Combined reference to FIGS. 5–8 shows that the auxiliary shelf 10 is pivotally connected to the upper end of the auxiliary shelf legs 13, 13' to enable the shelf 10 to be shifted between a storage position generally parallel to the auxiliary shelf legs 13, 13' (FIG. 7) and an in-use position almost perpendicular thereto (FIGS. 5, 6 and 8). Hinge or pivot connection joints 68, 68' securely connect the shelf 10 to the tops of the shelf legs 13, 13', and yet permit the shelf to rotate through approximately 270° from the vertical position seen in FIG. 7 to the use position illustrated in FIGS. 5, 6, and 8. The directional arrows in FIGS. 6 and 7 show the directions of rotation for the shelf 10 as well as the up-and-down movement of which the legs 13, 13' (and thus the shelf 10) is capable. The counter-rotation forward (i.e. counter-clockwise in FIGS. 6, 7) of the shelf 10 is arrested when the bottom of the shelf 10 comes into supportive contact with the top of the horizontal shelf support rod 66. As seen in the figures, particularly FIG. 5B, it is preferable that the pivot connection joints 68, 68' be offset rearwardly by means of offset arms 71, 71', so that the bottom of the shelf contacts the support rod 66 at a point in vertical alignment with the shelf legs 13, 13'.

Figure 5B:
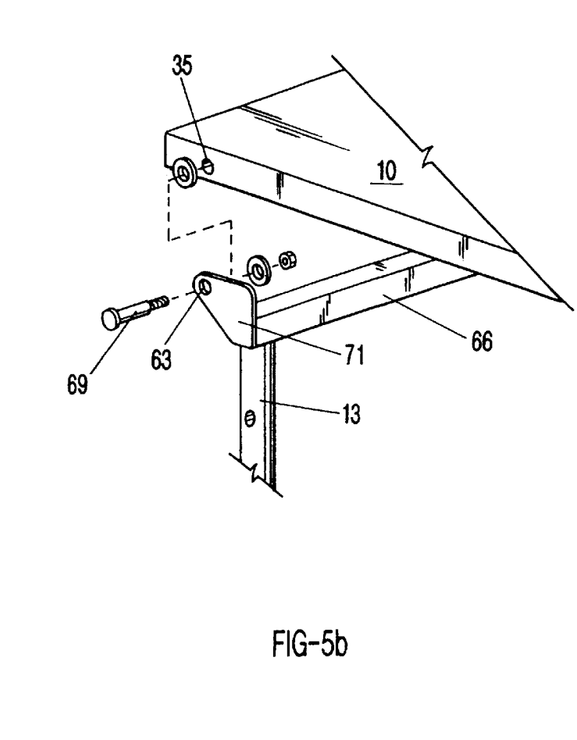
FIG. 5B is an enlarged exploded view of another portion of the embodiment shown in FIG. 5.

FIG. 5B more specifically depicts a preferred configuration whereby the auxiliary shelf 10 is pivotally connected to the shelf legs 13, 13'. The respective top ends of each of the shelf legs 13, 13' are rigidly attached to a horizontal cross bar 66 having a length running about equal to the length of the cart 11 and shelf 10. Vertical flanges defining offset arms 71, 71', extend rigidly upward from the ends of the cross bar 66. The flange of each offset arm 71 is penetrated by a hinge hole 63 which is alignable with a corresponding shelf hinge hole 35 in the end of the shelf 10. A hinge pin 69 insertable into the aligned holes may be secured in place by nuts and washers as shown, or by any other suitable known pin security. The hinged connection between the shelf 10 and the cross bar 66 defines the pivot connection joints 68, 68' which allow the shelf to be rotated around the bar 66 between the use position and a collapsed storage position.

FIG. 6, an end or right side view of the invention in use upon a conventional operating room cart 11, illustrates the auxiliary shelf 10 in the "use" position. FIG. 7 therefore shows the auxiliary shelf 10 in the stored position, generally vertical with respect to both the floor and the main shelf 12 (as also seen in FIG. 3). In the stored position, the auxiliary shelf 10 is nearly flush against the rear legs 15, 15' and thus is removed to an innocuous, space-saving location for storage while not in use. If desired, the main shelf 12 can be used while the auxiliary shelf is locked in the stored position. By way of further illustration, FIG. 8 shows a front view of the auxiliary shelf 10 and main shelf 12 in a position for use. It is preferable to provide wheel extensions 72, 72' as seen in FIG. 6 to compensate for the change in the center of gravity of the combination of auxiliary shelf 10 with the stock cart 11.

To fix the position of the auxiliary shelf legs 13, 13' in the vertical direction, a quick-release pin 61 movably mounted in each clamp block 60, 60' is engageable into any of a series of adjustment apertures 64, 64' running along the appropriate portion of the auxiliary shelf legs 13, 13', as described.

Reference is returned to FIG. 5 A, which shows the inclusion of a constant-spring assembly to provide a lift assist which reduces the operator's effort involved in lifting the auxiliary shelf 10 from the collapsed stored position to the use position. A constant-force spring assembly is provided in association with each of the mounting clamp assemblies 60, 60', whereby an operative connection between each shell leg 13, 13' and the immobile clamps 60, 60'. Description of one constant-force spring assembly describes the pair used on the inventive apparatus. The constant-force springs tend to urge the auxiliary shelf legs 13, 13' upward through the mounting clamps 60, 60'.

The constant-force spring 100, for example a reeled coil spring, is disposed within a bracket 102 fixedly secured to the mounting clamp 60. The constant-force coil spring 100 is reeled upon axle pin 103 which pin is rotatably mounted in the bracket 102. The outer free end of the spring 100 is connected to a horizontal rigid plate 106 (as by rivets or screws as indicated in FIG. 5A); the plate 106 is fixedly secured to the bottom end of the auxiliary shelf leg 13. Accordingly, when the auxiliary shelf 10 is pivoted up, over and around the bar 66 and into the vertical "collapsed" position, and the release pin 61 is removed, the shelf legs 13, 13' slide downward through the clamps 60, 60' into the low position seen in FIG. 7. As the legs 13, 13' slide down, each of the constant force springs 100 is paid out and unwound from its associated reel as the distance from the clamps 60, 60' to the bottoms of the corresponding) ones of the legs 13, 13' increases. The constant force spring 100 tends toward the wound-up position, such that the constant force spring 100 pulls upwardly (e.g. about 25 pounds force in each spring) on the bottoms of the leg 13 and thus to lift the shelf upward. The spring 100 does not completely overcome the weight force of the folded and collapsed auxiliary shelf, so that the shelf 10 remains in the collapsed storage position. However, the upward urging of the spring 100 allows a user of the invention to lift the shelf 10 up with a minimum of effort and less likelihood of injury.

Alternatively, in lieu of the constant force spring, the apparatus may provided with a gas spring lift-assists of conventional off-the shelf construction, extending between the lower end of each of the rear legs 15, 15' and the horizontal shelf support 66 which runs between the two shelf legs 13, 13'. Thus, the gas spring lift assists function, using controllably releasable confined gas or pressure, to regulate the rate of sliding movement of the legs 13, 13' through the clamp blocks 60, 60'. By gas pressure, the lift assists reduce the effort required to raise the auxiliary shelf 10, and also prevent sudden, slamming, downward collapse of the auxiliary shelf 10. Personnel operating the inventive apparatus thus can controllably and easily raise or lower the auxiliary shelf 10, as the auxiliary shelf legs 13, 13' slide smoothly and slowly within the clamp blocks 60, 60'.

Preferably, the shelf 10 when in the use position seen in FIGS. 5 and 6 and is not quite horizontal, but rather is slightly pitched or inclined (about five degrees or less) with the front of the shelf 10 being slightly higher above the main shelf 12 than the back (i.e. near the legs 13, 13') thereof. By slightly inclining the shell 10 when in the unloaded in-use position, when the shelf 10 is loaded for use, the weight of the items on the shelf will flex it a few degrees (i.e. counter-clockwise in FIG. 6) into a near-horizonital position. In this manner, the weight of materials upon the shelf 10 won't over-rotate the shelf 10 to the point that the items might slide forward off the auxiliary shelf 10 to drop onto the main shelf 12.

Figures 9, 10:
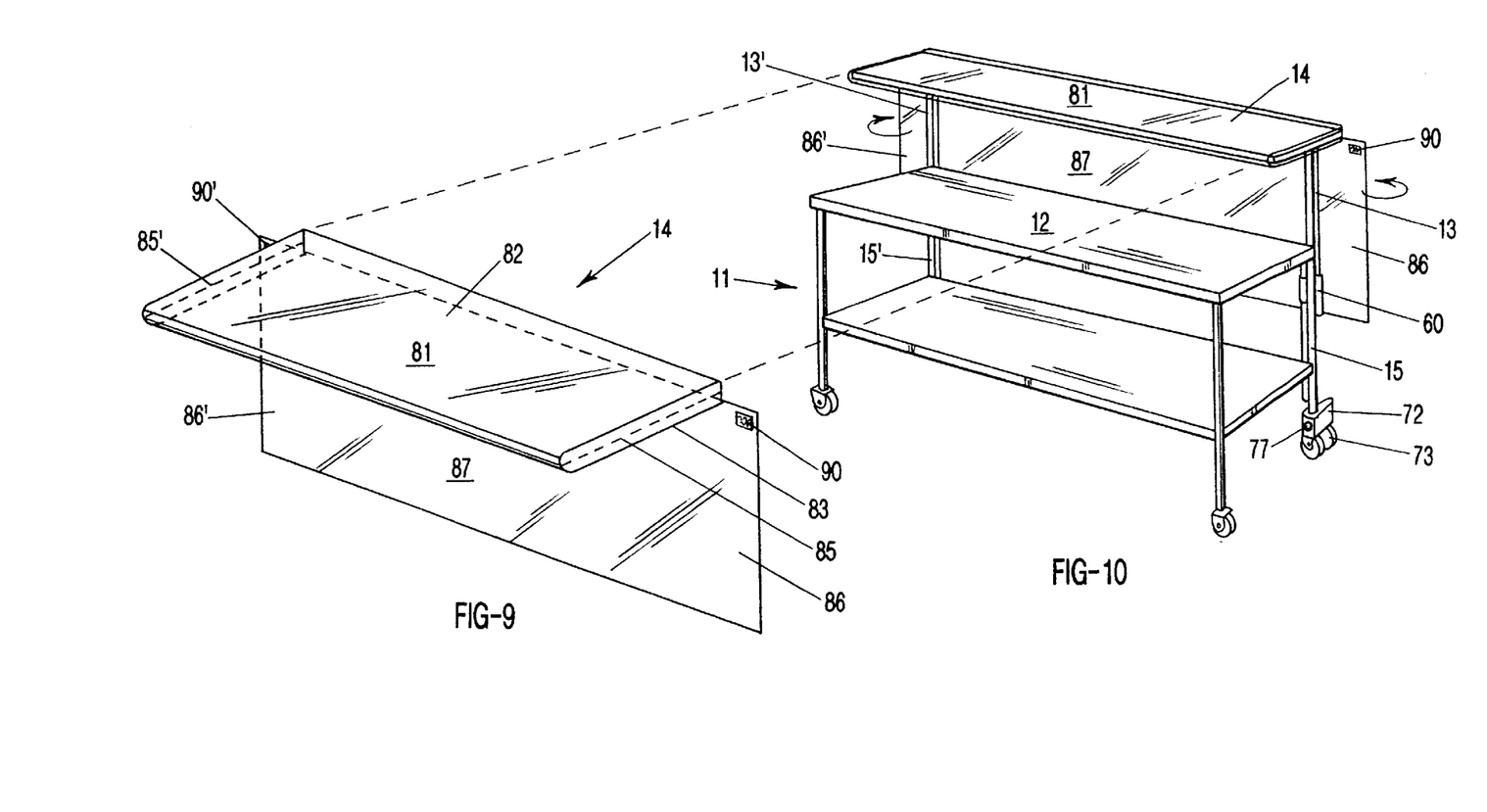
FIG. 9 is a perspective front view of a preferred embodiment of the drape component according to the present invention.
FIG. 10 is a front perspective view of the embodiment shown in FIG. 5, depicting the drape component in place upon the auxiliary shelf component.

FIGS. 6 and 7 illustrate that a leg extension 72, 72' with auxiliary support wheels 73, 73' is pivotally attached to the bottom ends of the rear main legs 15, 15'. The leg extensions 72, 72' are rotatable about the main legs 15, 15' between a retracted position as seen in FIG. 7 (contained within the imaginary rear plane of the cart 11) and an extended position (protruding from the rear plane of the cart 11) as seen in FIGS. 6 and 10. A tension knob 77, 77' is used to releasably fix the extensions 72, 72' against rotation. In the extended position, the extensions 72, 72' help provide additional stabilizing support to the cart 11 when the upper auxiliary shelf 10 is elevated and loaded in the use position. By turning the tension knobs 77, 77' to release the extensions 72, 72' to a pivotable condition, the extensions can be moved in to the retracted positions where they are tucked out of the way for storage.

FIGS. 9–11B show that the preferred embodiment of the invention includes a special sterile drape 14 custom-fitted to cover the auxiliary shelf 10. The drape 14 is fashioned from clear plastic sheeting. The clear plastic sheet of the drape 14 is doubled over against itself and its edges sealed along a seam 85 to define a pocket or slip-cover portion 81 which slides over the shelf 10 from the front thereof. A rear edge of the drape 14 is provided with double-sided adhesive strips so that the drape 14 may be removably affixed to the shelf in the position shown in FIG. 10. Also as shown, a substantial length of a main central portion 87 of the drape is free to hang from the pocket portion 81, and down between the shelf legs 13, 13' and the main table 12 to assist in maintaining the sterile field. Additional double-sided adhesive strips optionally are provided to removably affix the inventive drape 14 to any other drape (not shown) in use to cover the main shelf 12. An advantage of the invention is that the uppermost horizontal planar portion of the drape 14, the portion flush against and generally coextensive with the horizontal surface of the shelf 10, has a paper layer 91 above the plastic layer. The paper layer 91 is the uppermost layer when the drape 14 is in use, while the underlying layer of the clear plastic helps prevent undesirable "strike-through" of the drape (e.g. punctures through which bodily fluids may drain from used instruments sitting on the shelf 10), which compromises the sterile field. The drape 14 thus is convenient to use to cover the shelf 10, but may be disposed in the trash after use.

Thus, the use of a special drape 14 upon the auxiliary shelf 10 provides for a sterile operating field. The drape 14 is made from flexible clear vinyl or other suitable plastic, as described. The drape 80 has a pocket portion 81 comprised of an upper ply 82 doubled back over a lower ply 83 and joined thereto along the side seams 85, 85'. As illustrated in FIG. 11, the pocket portion 81 preferably includes an exterior paper layer 91 bonded to the upper ply 82 as ; previously described. The paper layer 91 is absorbent and helps prevent ruptures of the upper ply which may compromise field sterility. The pocket portion 81 can then be slipped over the shelf 10 from the front.

Figure 11A:
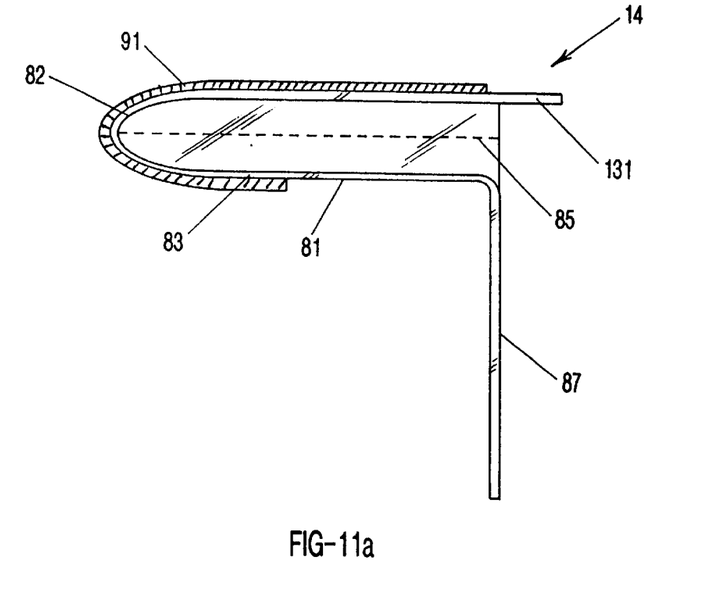
FIG. 11A is a side sectional view of the drape component of the invention seen in FIG. 9.
Figure 11B:
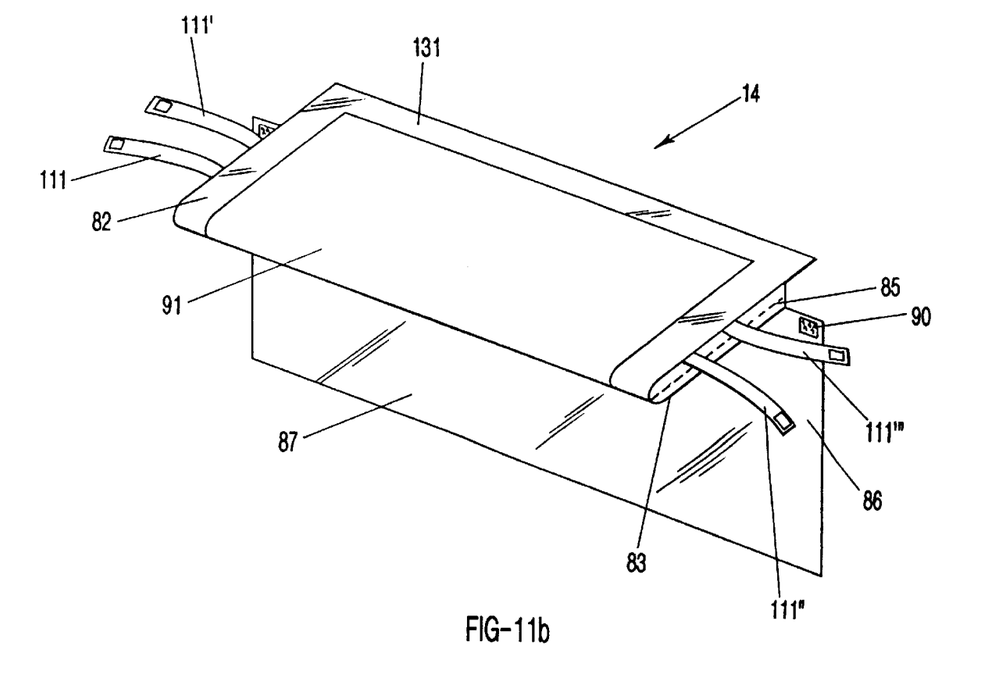
FIG. 11B is a top perspective view of the embodiment of the drape component depicted in FIG. 11A.

An advantage of the drape 14 is the provision of side flaps 86, 86' which extend laterally to the sides of the main vertical panel 87. The side flaps 86, 86' are provided with hook-and-loop fabric fasteners 90, 90', or other suitable fasteners. The flaps 86, 86' are or may be wrapped back around the auxiliary shelf legs 13, 13', as suggested by the directional arrows in FIG. 10, and then fastened by the fasteners 90, 90' to the back of the horizontal rod 66 to better maintain a sterile field while the auxiliary shelf 10 is in use and the leg extensions 72, 72' are extended. Also, as seen in FIG. 11B, the drape 14 may optionally be provided with tab straps 111, 111', 111", 111''', which permit the drape to be unfolded and manipulated into place upon the auxiliary shelf 10 without direct handling, thus promoting sterility of the drape's working surfaces. The may also be a back flap 131 provided as an extension of the top ply 82, which can be wrapped around the back of the auxiliary shelf and secured to the rear underside of the shelf 10 by means of two-way tape or other suitable adhesive.

Figure 12:
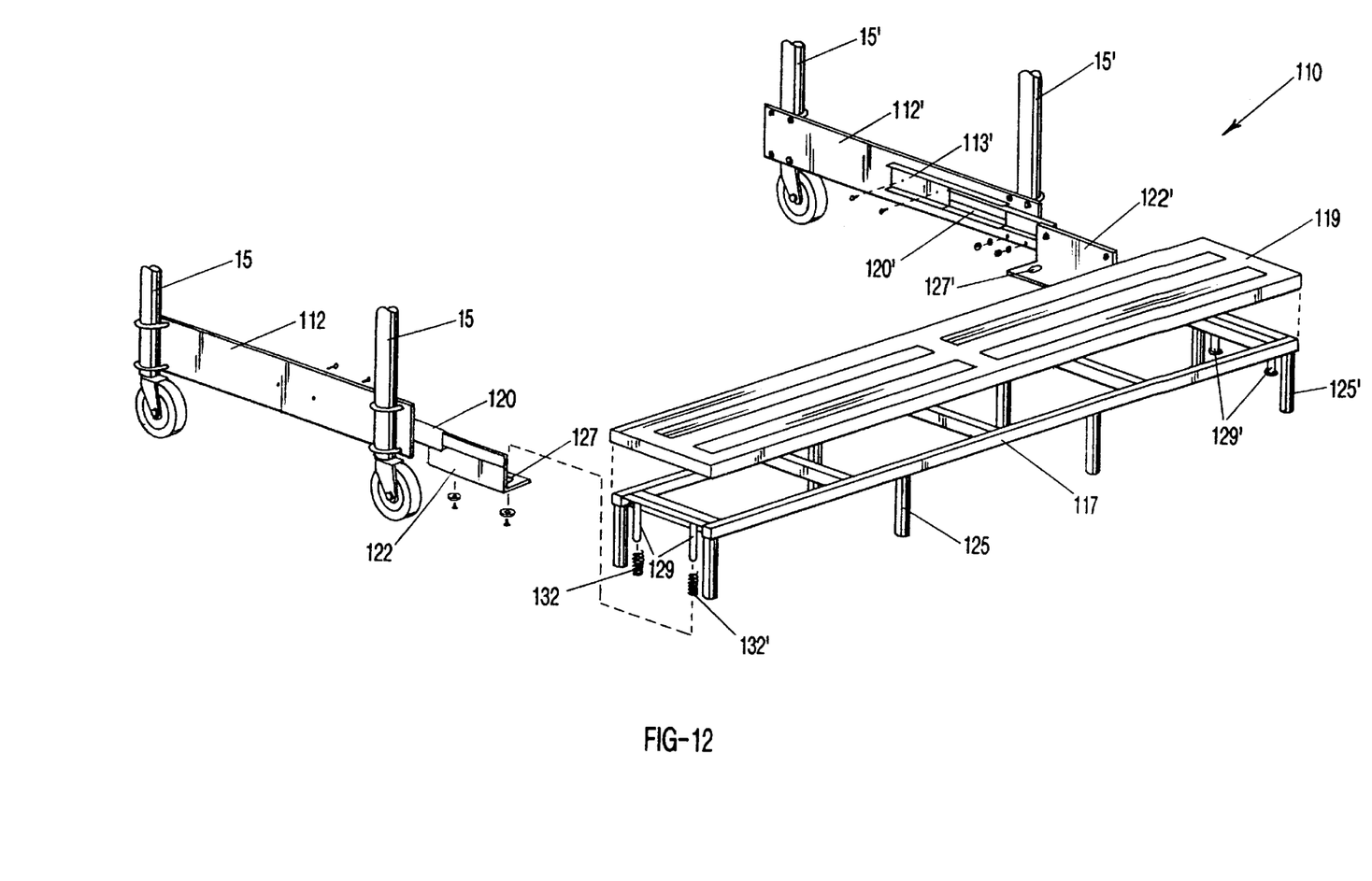
FIG. 12 is an exploded front perspective view of the step stair assembly according to the present invention.

FIG. 12 illustrates an optional pull-out step stair for use according to one embodiment of the invention. Like the auxiliary shelf 10, the step stair 110 assembly is configured to be attachable to existing operating room carts, and thus carts currently in use in operating rooms may be retrofitted with the step stair according to the invention. The step stair assists operating room personnel, particularly persons of short stature, easily to view and reach items resting upon the elevated auxiliary shelf 10 during surgery. An advantage of the invention is that the user can use his or her foot to deploy or retract the step stair 110, obviating the need to handle the step stair with the hands and thereby jeopardize their sterility.

As seen in FIG. 12, the step stair assembly is adapted for attachment to the main legs 15, 15' of a known type of cart, such as the cart 11 seen in FIG. 5. The step stair assembly includes the step stair frame 117 upon the top of which is permanently attached a non-skid tread 119. The frame 117, which may be manufactured from stainless steel, has a plurality of legs 125, 125' which contact the floor to support the step stair 110 while a person is standing thereon. By means of a cooperating arrangement of C-channels connected to the frame 117 and to mounting braces disposed upon the legs 15, 15' of the cart, the step stair 110 is slidably movable and positionable with respect to the cart. Rigid mounting braces 112, 112', fashioned for example form rolled stainless steel, are semi-permanently and very securely attached to the lower ends of the main legs 15. 15' so as to extend between respective end pairs 15, 15 and 15', 15' of main legs as seen in FIG. 12. Attachment may be by means of U-bolts and nuts or any other reliable, secure attachment. Bolts or welding or other extremely secure fastening means are used to fasten large C-channels 113, 113' (only one visible in FIG. 12) on the interior sides of each of the mounting braces 112, 112'. The immobile large C-channels 113, 113' are immovably disposed horizontally (i.e. parallel to the operating room floor) and so that their open mouths face away from the braces to which they are attached. A second pair of C-channels 120, 120' have exterior contours that correspond to the interior contours of the immobile Cchannels 113, 113', so that the sliding C-channels 120, 120' are slidable parallel to and engaged within the immobile C-channels 113, 113'. Thus, the pairs of C-channels 113, 120 and 113', 120' have complementary shapes, so that the movable C-channels 120, 120' are slidably disposed in, and held and guided by, the immobile C-channels 113, 113'. The pairs of Cchannels 113, 120 and 113', 120' cooperate so that the movable C-channels 120, 120' are capable of translational movement along a horizontal line only, but are otherwise restrained by immobile C-channels 113, 113' from any rotational movement, twisting, or vertical displacement.

Securely connected to the respective front ends of the movable C-channels 120, 120' are support brackets 122, 122' which are functionally integral to, and move with, the movable C-channels 120, 120' when the movable C-channels slide along and in the immobile C-channels 113, 113'. Support brackets 122, 122' have vertical flanges which are secured to the sliding C-channels 120, 120', and horizontal flanges which distend inwardly away from the mounting, braces 112, 112', as seen in the figure. Each of the horizontal flanges of the support brackets 122, 122' is penetrated by a pair of spindle holes 127, 127' (only one spindle hole in each bracket shown in FIG. 12). The spindle holes 127, 127' are sized and located to receive the pairs of spindles 129, 129' which extend downwardly from the top portions of the ends of the frame 117, as shown in FIG. 12.

At each end of the stair step frame 117 are provided a pair of downwardly extending spindles 129, 129' which are integral with or fixed to the frame. The spindles 129, 129' are sized with a diameter just slightly less than the diameter of the spindle holes 127, 127', so that the spindles can pass through the holes and move up and down within them. The spindles 129, 129' have lengths shorter than the lengths of the legs 125, 125' of the stair step 110, so that when the stair step legs 125, 125' touch the floor, the spindles do not reach to the floor. Coaxially disposed about each spindle 129, 129' is a coil spring 132, 132' having a diameter larger than the diameter of the spindle holes 127, 127'. Thus, the springs 132, 132' butt against the horizontal flanges of the support brackets 122, 122' when the spindles 129, 129' are inserted through corresponding ones of the spindle holes 127, 127'. When the step stair components are fully assembled, the weight of the frame 117 and the tread 119 compresses the springs 132, 132' between the bottom surface of the top of the frame 117 and the horizontal flange of the support brackets 122, 122'.

The stair step feature of the invention is assembled by slidably extending the C-channels 120, 120' and support brackets 122, 122' to the position seen in FIG. 5, and then lowering the frame 117 and tread 119 onto the support brackets 122, 122' so that both pairs of spindles 129, 129' are slidably inserted through corresponding pairs of spindle holes 127, 127' in the associated support brackets 122, 122', until the springs 132, 132' abut the top surfaces of the horizontal flanges of the brackets. The frame legs at the very ends of the frame 117 distend down past the axial ends of each of the brackets 122, 122'. Washers and nuts are then secured to the distal ends of the spindles 129, 129' to prevent the distal ends of the spindles from complete withdrawal from the spindle holes, thus movably attaching the frame 117 to the brackets 122, 122'. It is seen that when thus assembled, the frame 117 and tread 119 constituting the step stair 110 is movable up and down with respect to the support brackets 122, 122', as the spindles 129, 129' slide vertically up and down in the spindle holes 127, 127'. The engagement of the spindles 129, 129' in the holes 127, 127', however, limits the step stair 110 to only this up-and-down translation with respect to the brackets 122, 122'.

The springs 132, 132' act to lift the legs 125, 125 of the step stair 110 clear off the floor unless someone is standing upon the tread 119. The springs 132, 132' are in compression between the horizontal flanges of the brackets 122. 122' and the frame 117 due to the weight of the step stair 110, but the springs have a high enough spring coefficient that the force of the compressed springs urges the step stair upward by pressing against the brackets 122, 122' and the frame 117. The bias or urging force of the springs is adequate to overcome the weight of the step stair 110 thus to lift the step stair 110 high enough the distal ends of the legs 125, 125' are lifted free of the floor. Only when a person or other object of considerable weight is upon the step stair tread 119 is the compressive force of the springs 132, 132' overcome, causing the spindles 129, 129' to shift downward in the spindle holes 127, 127' a distance such that the ends of the legs 125, 125' engage the floor and thus support the person standing thereon.

The operation of the step stair aspect of the invention is apparent from the foregoing, but will be briefly described. FIG. 5 depicts the step stair assembly in the extended "use" position. When the stair step 110 is not in use, it can be moved into a stored position by sliding (as with the user's foot pushing against the tread 119) the sliding C-channels 120, 120' along and within the immobile C-channels 113, 113' and toward the back of the cart (e.g. from right to left in FIG. 5) until sliding C-channels have obtained their maximum distance of travel and the step stair 110 is ensconced under the cart and between the front lower cart legs 15, 15'. The engagement of the sliding C-channels 120, 120' in the immobile C-channels 113, 113' supports and guides this sliding movement of the step stair 110. The step stair 110 is free to so move, as the force of the springs 132, 132' lifts the legs 125, 125' free of the floor so that the step stair is supported above the floor solely by the cooperation of the sliding C-channels 120, 120' with the immobile C-channels 112, 113'.

When the user desires to make use of the step stair 110, she may retract it from under the cart by simply catching the frame 117 with the top of her shoe, and pulling outward. The sliding C-channels 120, 120' slide along and within the immobile C-channels 113, 113', while the cooperation of the engaged pairs of C-channels hold the step-stair 110 above and clear of the floor. Conventional stops (not shown) prevent the sliding C-channels 120, 120' from sliding completely clear out of the immobile C-channels 113, 113'. When the sliding Cchannels 120, 120' reach the end of their outward travel, the step stair 110 is in the extended use position seen in FIG. 12. The user can then step upon the tread 119, at which time her weight compresses the springs 132, 132', and the spindles 129, 129' plunge down through the spindle holes 127, 127' and guide the downward movement of the frame 117 until the legs 125, 125' of the step stair 110 contact the floor. The user then stands upon the tread 119, her weight supported entirely by the legs 125, 125'. When the user steps off the tread 119, the springs 132, 132' again lift the legs 125, 125' clear of the floor, and the step stair 110 is ready to by pushed with the foot to slide back into the retracted stored position. Notably, since the legs 125, 125' of the step stair 110 do not touch the ground when the step stair is retracted and not in use, the wheeled cart upon which the step stair assembly is mounted can be freely wheeled about.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An auxiliary shelf apparatus for use in combination with an operating room cart having at least two lower legs, said auxiliary shelf apparatus comprising:

a pair of shelf legs, each said leg having an upper end and a lower end;

a horizontal shelf support rod extending between said upper ends of said shelf legs;

a clamp on each of said shelf legs for clamping each of said shelf legs parallel to a respective one of the cart lower legs, said shelf legs slidably disposable through each of said clamps;

a planar shelf;

a pair of pivot joints pivotally connecting a back edge of said shelf to the respective upper ends of said shelf legs, said pivot joints offset rearwardly from said upper ends;

an aperture in each of said clamps;

a plurality of uniformly spaced holes in said shelf legs, any one of said holes alignable with said aperture in said clamp;

a pair of pins, each of said pins insertable into said aperture and into a selected one of said holes aligned with said aperture, thereby to adjust and maintain the vertical position of said shelf; and means, operably connected between said shelf legs and said lower legs, for biasing said shelf legs upward;

wherein said shelf is selectively pivotable between a horizontal position above the cart, wherein said shelf contacts and is supported by said shelf support rod, and a vertical, collapsed storage position parallel to said lower cart legs.

2. An apparatus according to claim 1 wherein said means for biasing comprises at least one member selected from the group consisting of constant spring assemblies, pneumatic lifts.

3. An apparatus according to claim 1 further comprising a drape useable in combination with said shelf, said drape comprising a portion doubled over against itself and having edges sealed along a seam to define a pocket portion slidable over said shelf when said shelf is in the horizontal position.

4. An apparatus according to claim 3 wherein said drape further comprises a main central portion hangable from said pocket portion and down between said shelf legs.

5. An apparatus according to claim 4 further comprising:

side flaps extending laterally from sides of said central portion, said flaps wrappable around said shelf legs; and means for fastening said flaps to the back of said shelf support rod.

6. An apparatus according to claim 3 wherein said pocket portion comprises an uppermost horizontal planar portion disposable flush against and substantially coextensive with a horizontal surface of said shelf, said horizontal planar portion having a paper layer disposed upon a plastic layer.

7. An auxiliary shelf apparatus for use in combination with an operating room cart having at least two lower legs, said auxiliary shelf apparatus comprising:

a pair of shelf legs, each said leg having an upper end and a lower end;

a horizontal shelf support rod extending between said upper ends of said shelf legs;

means for releasably attaching each of said shelf legs to a respective one of said cart lower legs;

a planar shelf;

a pair of pivot joints pivotally connecting a back edge of said shelf to the respective upper ends of said shelf legs, said pivot joints offset rearwardly from said upper ends;

means for adjusting the vertical position of said shelf;

means, operably connected between said shelf legs and said lower legs, for biasing said shelf legs upward;

wherein said shelf is selectively pivotable between a horizontal position above the cart wherein said shelf contacts and is supported by said shelf support rod, and a vertical, collapsed storage position parallel to said lower cart legs.

8. An apparatus according to claim 7 wherein said means for releasably attaching comprises a clamp on each of said shelf legs for clamping each of said shelf legs parallel to a respective one of the cart lower legs, wherein said shelf legs are slidably disposable through each of said clamps.

9. An apparatus according to claim 7 wherein said means for adjusting comprises:

an aperture in each of said clamps;

a plurality of uniformly spaced holes in said shelf legs, any one of said holes alignable with said aperture in said clamp;

a pair of pins, each of said pins insertable into said aperture and into a selected one of said holes aligned with said aperture, thereby to adjust and maintain the vertical position of said shelf.

10. An apparatus according to claim 7 wherein said means for biasing comprises at least one member selected from the group consisting of constant spring assemblies, pneumatic lifts.

11. An apparatus according to claim 7 further comprising a drape useable in combination with said shelf, said drape comprising a portion doubled over against itself and having edges sealed along a seam to define a pocket portion slidable over said shelf when said shelf is in the horizontal position.

12. An apparatus according to claim 11 wherein said drape further comprises a main central portion hangable from said pocket portion and down between said shelf legs.

13. An apparatus according to claim 12 wherein said pocket portion comprises an uppermost horizontal planar portion disposable flush against and substantially coextensive with a horizontal surface of said shelf, said horizontal planar portion having a paper layer disposed upon a plastic layer.

14. An apparatus according to claim 13 further comprising:

side flaps extending laterally from sides of said central portion, said flaps wrappable around said shelf legs; and means for fastening said flaps to the back of said shelf support rod.

* * * * *